United States Patent
Clarke et al.

(10) Patent No.: US 7,000,770 B2
(45) Date of Patent: Feb. 21, 2006

(54) PACKAGING FOR STENTS AND STENT DELIVERY SYSTEM

(75) Inventors: Frank Clarke, Turloughmor (IE); Thomas Farrell, Claregalway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/688,459

(22) Filed: Oct. 16, 2003

(65) Prior Publication Data

US 2004/0187438 A1    Sep. 30, 2004

(30) Foreign Application Priority Data

Mar. 25, 2003    (IE)    ............... PCT/IE03/00046

(51) Int. Cl.
*A61M 25/00*    (2006.01)
(52) U.S. Cl. ...................... 206/571; 364/438
(58) Field of Classification Search ........... 206/204, 206/205, 213.1, 363–370, 438–441, 570–572
See application file for complete search history.

(56) References Cited

U.S. PATENT DOCUMENTS

| 4,216,860 A | | 8/1980 | Heimann |
| 4,406,363 A | * | 9/1983 | Aday ..................... 206/63.3 |
| 4,496,052 A | * | 1/1985 | Nertman ................. 206/470 |
| 4,519,501 A | * | 5/1985 | Cerwin ................... 206/339 |
| 4,730,726 A | * | 3/1988 | Holzwarth ............... 206/204 |
| 4,928,830 A | * | 5/1990 | Brewer ................... 206/570 |
| 5,318,543 A | * | 6/1994 | Ross et al. ............ 604/170.01 |
| 5,590,778 A | * | 1/1997 | Dutchik .................. 206/439 |
| 5,848,691 A | * | 12/1998 | Morris et al. ........... 206/364 |

FOREIGN PATENT DOCUMENTS

| EP | 0492399 A2 | 7/1992 |
| EP | 0782868 A1 | 7/1997 |
| WO | WO 9747349 A1 | 12/1997 |

* cited by examiner

*Primary Examiner*—Mickey Yu
*Assistant Examiner*—Jerrold Johnson

(57) ABSTRACT

A package for a drug-coated stent includes a tray adapted to receive a coiled stent delivery system and a pouch adapted to receive the tray and coiled stent delivery system. The tray contains at least one recess adapted to retain an oxygen or moisture scavenger pack.

6 Claims, 3 Drawing Sheets

PACKAGING FOR STENTS AND STENT DELIVERY SYSTEM

FIELD OF THE INVENTION

The present invention relates to a packaging system for drug-coated or treated stents and a method of packaging stents which minimise the level of exposure of the stents to oxygen, moisture and light and at the same time prevent oxygen and moisture scavenger packs touching the stent or delivery system.

BACKGROUND TO THE INVENTION

Cardiovascular disease, including atherosclerosis, is the leading cause of death in the U.S. A number of methods and devices for treating coronary heart disease have been developed, some of which are specifically designed to treat the complications resulting from atherosclerosis and other forms of coronary arterial narrowing.

One method for treating atherosclerosis and other forms of coronary narrowing is percutaneous transluminal coronary angioplasty, hereinafter referred to as "angioplasty" or "PTCA". The objective in angioplasty is to enlarge the lumen of the affected coronary artery by radial expansion. This is generally accomplished by inflating a balloon within the narrowed lumen of the affected artery. The wall of the artery itself may also be stretched as the balloon is inflated. With simple angioplasty, the balloon is threaded through the artery with a catheter and inflated at the place where the blood vessel is blocked. After the procedure, the balloon is then removed. With simply angioplasty alone, arteries may close up again or re-narrow. This narrowing is known as restenosis.

To reduce the risk of restenosis, a stent may also be inserted during angioplasty. A stent is a tube, often made of metals or occasionally plastic materials that is inserted into a vessel or a passage in the body to keep the lumen of the vessel open and to prevent closure due to a stricture or external compression. The use of a stent may reduce the risk of restenosis. However, stent insertion can cause undesirable reactions such as inflammation, infection, thrombosis, or proliferation of cell growth that occludes the passageway.

Restenosis occurs because the blood vessel wall is injured when the stent is implanted. The area then becomes inflated and new cells form scar tissue. The arterial walls may become so thick in some instances that they sometimes protrude into the mesh of the stent. In such cases, a further angioplasty may be undergone, and a new stent may be placed inside the existing one. If restenosis continues, the eventual alternative may be bypass surgery.

Alternatively, a treated stent may be inserted during the angioplasty. Such a treated stent may eliminate the need for repeat angioplasties and could spare some patients the trauma, risk and prolonged recovery associated with heart bypass surgery. The treated stent contains a therapeutic agent to assist in preventing restenosis. The coatings are bioengeered to release doses of the therapeutic agent and may or may not be contained on a coating on the stent. Agents contemplated act to stop new cells from forming without impairing the healing of the vessel. Agents may also dampen inflammation and have antibiotic properties.

However, because the treated stent comprises a therapeutic drug, treated stents present problems associated with drug administration. For example, for a drug to be administered effectively, the integrity of the drug's effective dosage should be maintained. Certain drugs require regulated conditions for efficacy, such as regulated air circulation or lack thereof, regulated exposure to light and oxygen.

Prior art packaging systems for coated stents have typically comprised a thermoform tray insert in a foil pouch, or a thermoform tray having a Tyvek™ lid in a foil pouch, into which the stent is vacuum packed. Such conventional packaging for stents do not provide for regulation of ambient conditions such as circulation of air or exposure to light and oxygen. Without such appropriate regulation, the efficacy of the drug and/or drug coating maybe reduced. Moreover, these packages tend to be heavier than those of the present invention, they utilise more material and they require more operator handling time to pack and so are more labour intensive to produce.

OBJECT OF THE INVENTION

It is thus an object of the present invention to provide a package which optimises ambient conditions for treated stents. It is also an object to provide a package for treated stents and their associated delivery systems, which allows the inclusion of oxygen and moisture absorbing agents within the sealed package but which prevents the absorbing agents touching the stent or delivery system so that no residue can be left on the stent or delivery system. The package must also be suitable for sterilisation by conventional techniques such as ethylene oxide (EtO) and gamma irradiation.

SUMMARY OF THE INVENTION

According to the present invention there is provided a package for a drug-coated stent comprising a tray adapted to receive a coiled stent delivery system and a pouch adapted to receive the tray and coiled stent delivery system, the tray containing at least one recess adapted to retain an oxygen or moisture scavenger pack.

The tray may be provided with channels into which the coils of the coiled stent delivery system can be located.

The package may further comprise a lid engagable with the tray and adapted to retain the scavenger pack in the recess in the tray and in communication with the internal environment of the pouch.

The tray may also comprise a pair of recesses adapted to retain a pair of scavenger packs. In particular the tray may comprise a pair of recesses adapted to retain oxygen and/or moisture scavenger packs, and the lid may comprise two apertures which overlie the recesses in the tray base when the lid and tray base are fitted together.

The lid and tray may be a snap fit together. The lid may be provided with a plurality of lugs which extend from the face of the lid which would overlie the tray base when the package is assembled, the tray base being provided with a plurality of cavities into which the lugs of the lid fit when the package is assembled.

BRIEF DESCRIPTION OF THE DRAWINGS

The invention will now be described in greater detail with reference to the accompanying drawings in which.

DETAILED DESCRIPTION OF THE DRAWINGS

Figure 1:
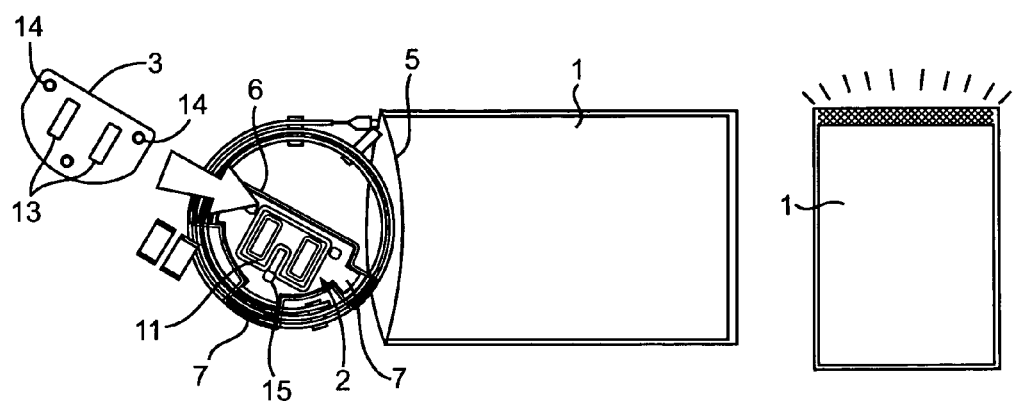
FIG. 1 shows a packaging system in accordance with the invention, with the treated stent and delivery system loaded on a tray base and the tray lid and absorber packs in exploded view.
Figure 2A:
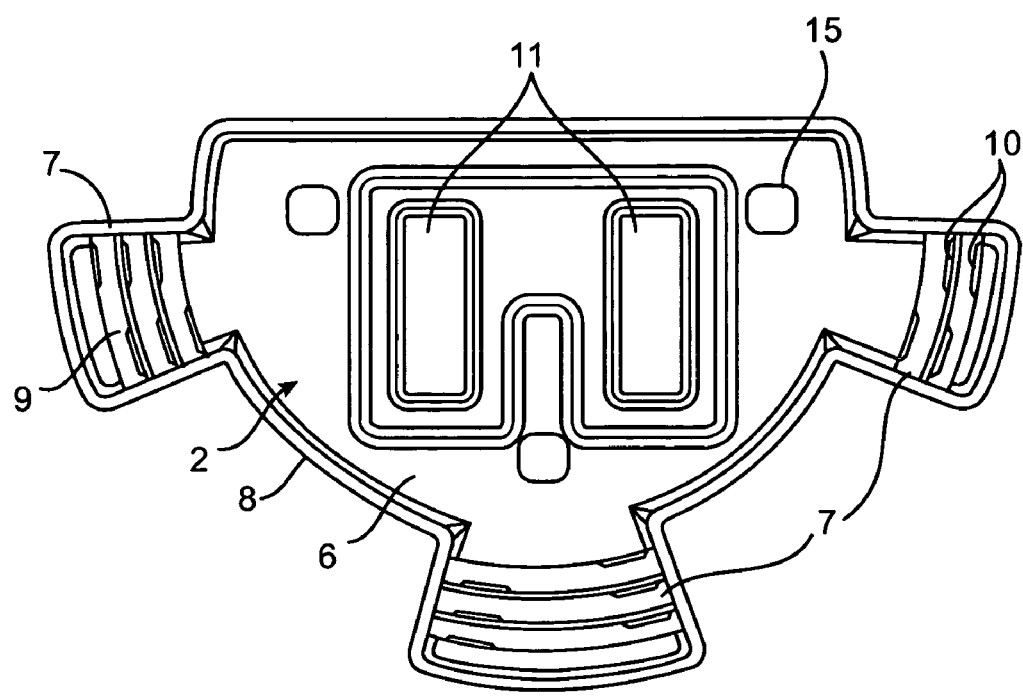
FIG. 2 shows the tray base in greater detail.
Figure 2B:
Figure 3A:
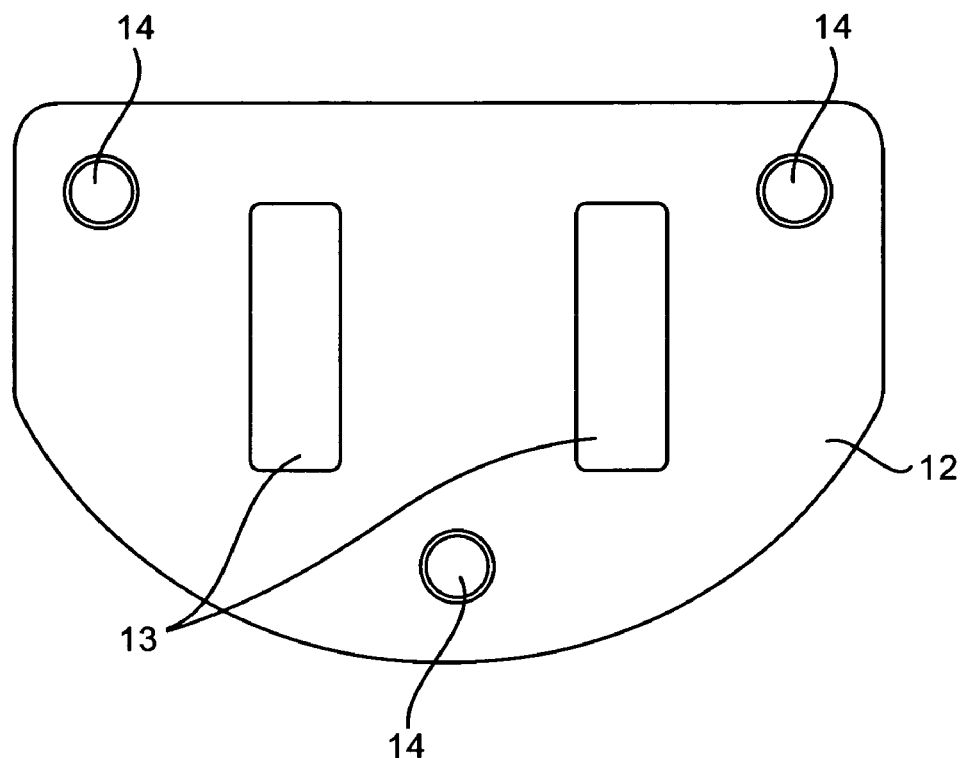
FIG. 3 shows the tray lid in greater detail.
Figure 3B:
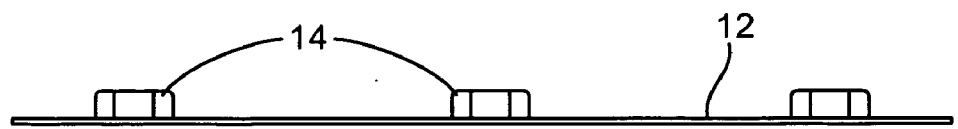

As shown in FIG. 1, the packaging system for a treated stent delivery system takes the form of a pouch or bag (1), a tray base (2) and a tray lid (3). The pouch (1) is formed from two layers of laminated foil (5) which are sealed together. A suitable foil is that available from Perfecseal Ltd. under the trade name 35781-G. The tray base and lid are produced by thermoforming from GPET co-polyester in a conventional manner. A suitable thickness for the tray base and lid is about 0.64+/−0.04 mm.

The tray base (2) has a body portion (6) which is of generally semi-circular configuration with three arms (7) which extend outwardly from the outer circumferential edge (8) of the tray base (2). These arms (7) are formed with a series of channels or grooves (9) which extend along the arm (7) parallel to the circumference of the semi-circular body portion (6) and would be concentric with the tray base (2) if it were a complete circle. The channels (9) are thus curved in the plane of the tray base (2). The channels (9) are adapted to receive the coils of a coiled stent delivery system and are provided at regular intervals along their course, with tabs (10) which serve to hols the delivery system within the channels (9).

The body portion (6) of the tray base (2) is also provided with two recesses (11) adapted to receive moisture and/or oxygen absorber or scavenger packs. Suitable oxygen and moisture absorber packs are commercially available from Mitsubishi Gas chemical company, Inc./(Pharmakeep KD-20™), and Silgel Ltd./(4 g Molecular Sieve sachets), respectively.

The packaging system also comprises a tray lid (12) which is of generally semi-circular configuration and which is a snap fit with the tray base (2). The lid (12) has two apertures (13) which, when the lid (12) is fitted onto the tray base (2) overly the recesses (11) which hold the absorber packs. Thus when the stent and delivery system are packaged on the tray base (2) with the lid (12) in place, and placed in the pouch (1), the absorber packs are in contact with the internal pouch environment via the apertures (13) in the lid (12). The absorber packs are thus ideally placed to scavenge oxygen and moisture within the pouch, but cannot touch the stent or delivery system.

The tray lid (12) is provided with three lugs (14) on the surface of the lid (12) which abuts the tray base (2) when the lid and base are assembled together. These lugs (14) are engageable with three cavities (15) in the tray base (2) so that the lugs (14) and cavities (15) together provide a snap-fit mechanism for the lid and tray base.

The advantage of not putting the absorber packs into direct contact with the delivery system is that there is a possibility that tiny amounts of content residue would be present on the outside of each pack, and this residue would adversely interact with the drug or other coating on the stent.

EXAMPLE 1

The process for packaging a stent comprises placing the drug-coated stent, mounted on a delivery system and loaded into a coiled dispenser onto the tray base so that the coils of the delivery system rest within the channels or grooves on the tray base. The scavenger packs are then placed within the recesses and the tray lid is snapped into place. The delivery system mounted on the tray is then placed in the pouch, as shown in FIG. 1.

In a single operation the open end of the pouch is flushed with nitrogen and vacuum-sealed, so that the two edges of the pouch are sealed together.

The inert gas used to flush the package is preferably nitrogen. The nitrogen is flushed for between 1 and 10 seconds at a pressure of 10 to 30 psi. The vacuum draw down time is suitably 1 second, up to 10 seconds. The package may be sealed by clamping the edges of the package between upper and lower jaws of a sealing device. The seal time may be from 1 to 10 seconds, with an upper jaw seal temperature of 110 to 200° C. and a lower jaw seal temperature of 60 to 100° C. and the seal pressure may be from 30 to 100 psi.

The sealed pouch is then sterilised by gamma radiation in a conventional manner.

EXAMPLE 2

The process for packaging a stent which is sterilised by ethylene oxide is slightly different. In this embodiment the Treated stent mounted on a delivery system and loaded onto a coiled dispenser, is placed in the tray, with the scavenger packs in place, and the lid is put in place. The tray is then placed in a pouch formed from one layer of a breathable membrane and one layer of a foil material. The breathable provides an entry and exit point for the ethylene oxide gas in the sterilisation process. The pouch containing the loaded tray is then sealed at its open end. The sealing temperature is 140–160° C., the pressure is 90–100 psi and the dwell time is approximately 1–2 sec. The package is then sterilised using ethylene oxide in a conventional manner. After sterilisation the pouch is then vacuum-sealed within an outer all foil pouch following flushing with nitrogen.

The words "comprises/comprising" and the words "having/including" when used herein with reference to the present invention are used to specify the presence of stated features, integers, steps or components but does not preclude the presence or addition of one or more other features, integers, steps, components or groups thereof.

What is claimed is:

1. A package for a drug-coated stent comprising a coiled dispenser for receiving a stent delivery system,
   a tray having a base and a lid, the base having at least one recess adapted to retain an oxygen or moisture scavenger pack within the tray and in communication with the internal environment of the tray and having channels for receiving the coiled dispenser and the lid having an aperture that overlies the at least one recess when the lid and tray base are fitted together;
   at least one oxygen or moisture scavenger pack in the at least one recess;
   and a pouch adapted to receive the tray and coiled dispenser.

2. A package as claimed in claim 1 comprising a pair of recesses adapted to retain a pair of scavenger packs within the tray and in communication with the internal environment of the pouch.

3. A package as claimed in claim 1 comprising a pair of recesses adapted to retain oxygen and/or moisture scavenger packs, the lid comprising two apertures which overlie the recesses in the tray base when the lid and tray base are fitted together.

4. A package as claimed in claim 1 wherein the lid and tray are secured with a snap fit.

5. A package as claimed in claim 4, wherein the lid is provided with a plurality of lugs which extend from the face of the lid which would overlie the tray base when the package is assembled, the tray base being provided with a plurality of cavities into which the lugs of the lid fit when the package is assembled.

6. A package as claimed in claim 1 wherein the pouch is made of a plastics covered foil.

* * * * *